United States Patent
Andres et al.

(10) Patent No.: US 8,541,746 B2
(45) Date of Patent: Sep. 24, 2013

(54) PROCESS AND SYSTEM FOR THE NONDESTRUCTIVE QUALITY DETERMINATION OF A WELD SEAM, AND A WELDING DEVICE

(75) Inventors: Thorsten Andres, Paderborn (DE); Sven Przybylski, Paderborn (DE)

(73) Assignee: Benteler Automobiltechnik GmbH, Paderborn (DE)

( * ) Notice: Subject to any disclaimer, the term of this patent is extended or adjusted under 35 U.S.C. 154(b) by 772 days.

(21) Appl. No.: 12/620,176

(22) Filed: Nov. 17, 2009

(65) Prior Publication Data
US 2010/0123080 A1    May 20, 2010

(30) Foreign Application Priority Data
Nov. 20, 2008  (DE) .......................... 10 2008 058 187

(51) Int. Cl.
*G01N 21/88*    (2006.01)

(52) U.S. Cl.
USPC ............. 250/341.6; 250/341.1; 250/336.1; 250/338.1; 250/339.04; 250/339.14; 250/342

(58) Field of Classification Search
USPC ........................................ 250/341.1, 341.6
See application file for complete search history.

(56) References Cited

U.S. PATENT DOCUMENTS

| | | | | |
|---|---|---|---|---|
| 4,153,832 A * | 5/1979 | Iio et al. | | 219/124.34 |
| 4,410,381 A * | 10/1983 | Chapman, II | | 156/64 |
| 4,817,020 A * | 3/1989 | Chande et al. | | 702/135 |
| 5,225,883 A * | 7/1993 | Carter et al. | | 356/45 |
| 5,292,195 A * | 3/1994 | Crisman, Jr. | | 374/4 |
| 5,360,960 A * | 11/1994 | Shirk | | 219/121.83 |
| 5,502,292 A * | 3/1996 | Pernicka et al. | | 219/121.64 |
| 5,651,903 A * | 7/1997 | Shirk | | 219/121.64 |
| 5,714,734 A * | 2/1998 | Peterson et al. | | 219/130.21 |
| 6,137,860 A * | 10/2000 | Ellegood et al. | | 378/58 |
| 6,153,848 A * | 11/2000 | Nagae et al. | | 219/110 |
| 6,414,261 B1* | 7/2002 | Maetschke | | 219/109 |
| 6,585,146 B2* | 7/2003 | Shepard | | 228/104 |
| 6,829,263 B1* | 12/2004 | Richter et al. | | 372/36 |
| 7,220,966 B2* | 5/2007 | Saito et al. | | 250/341.6 |
| 7,479,616 B2* | 1/2009 | Wang et al. | | 219/121.64 |
| 2002/0134817 A1* | 9/2002 | Shepard | | 228/105 |
| 2006/0006156 A1* | 1/2006 | Huonker et al. | | 219/121.64 |
| 2006/0011592 A1* | 1/2006 | Wang et al. | | 219/121.64 |
| 2007/0237201 A1* | 10/2007 | Ignatowicz | | 374/7 |
| 2010/0086003 A1* | 4/2010 | Pfitzner et al. | | 374/5 |
| 2010/0134628 A1* | 6/2010 | Pfitzner et al. | | 348/159 |

* cited by examiner

*Primary Examiner* — David Porta
*Assistant Examiner* — Djura Malevic
(74) *Attorney, Agent, or Firm* — Barnes & Thornburg LLP

(57) ABSTRACT

A process for the non-destructive determination of the quality of a weld seam, the process steps comprising: providing a first and a second component; connecting the first and second components by a weld seam produced by a welding operation; and measuring a surface temperature of the weld seam and surface temperatures of areas of the first and second components adjacent to the weld seam that were heated by the welding operation. A system for carrying out the process for the non-destructive determination of the quality of a weld seam, the system comprising: a measuring device, an analyzing unit, and a welding device.

7 Claims, 2 Drawing Sheets

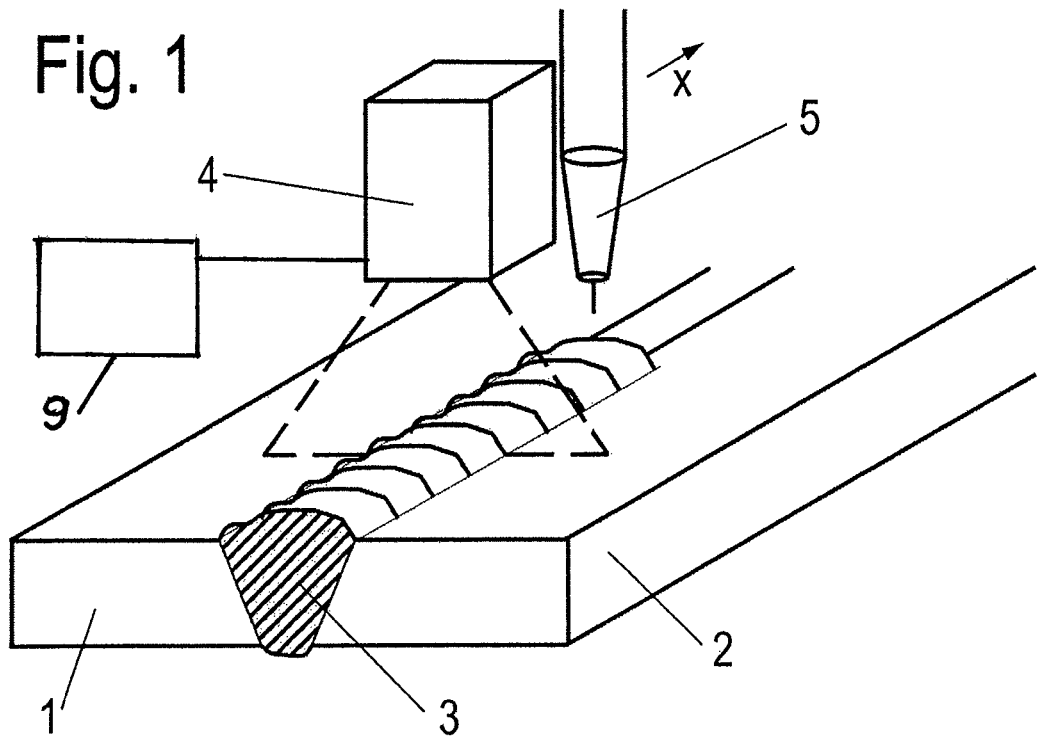
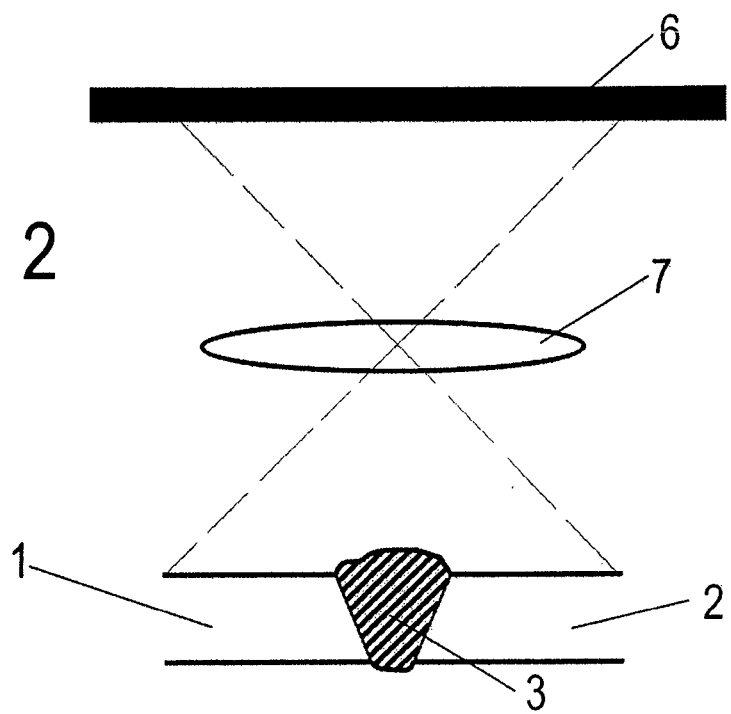

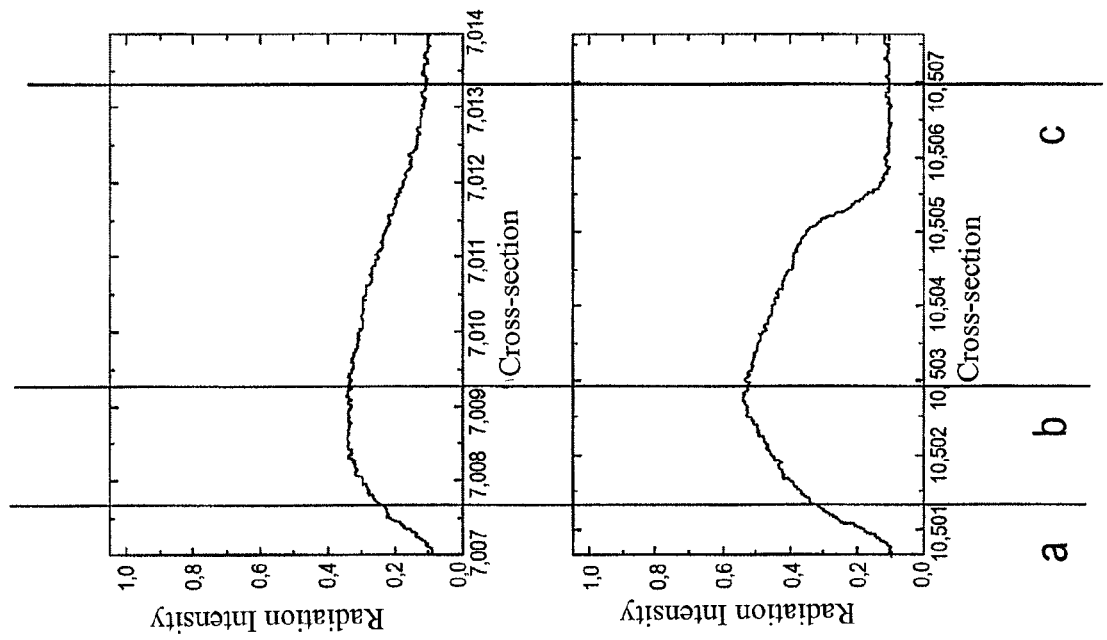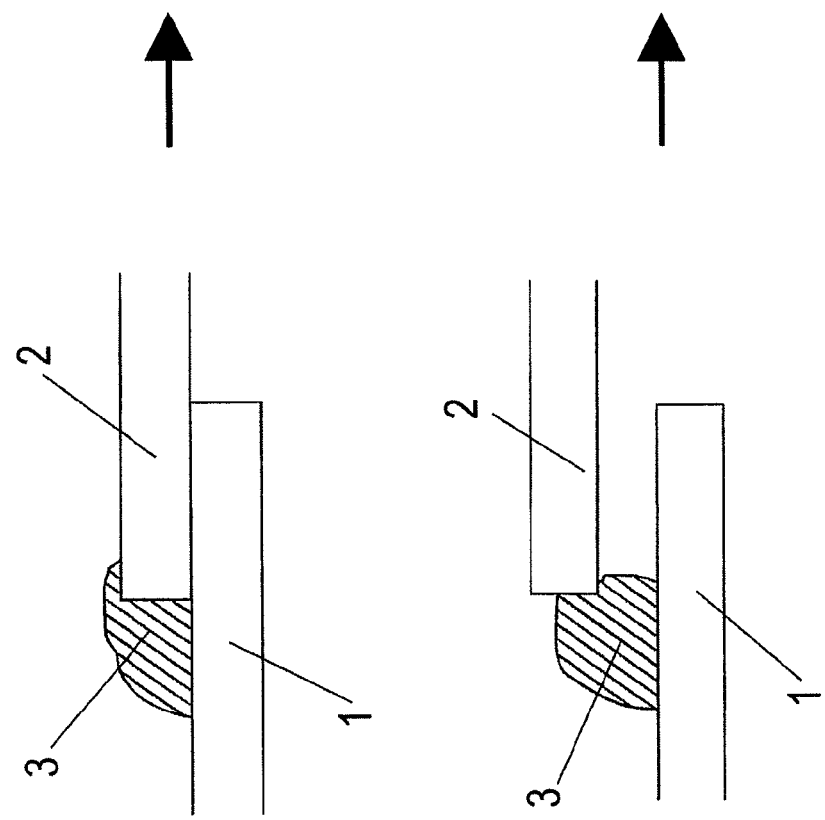
Fig. 3

PROCESS AND SYSTEM FOR THE NONDESTRUCTIVE QUALITY DETERMINATION OF A WELD SEAM, AND A WELDING DEVICE

CROSS-REFERENCE TO RELATED APPLICATIONS

This application claims the benefit of priority to German Patent Application No. DE 10 2008 058 187.9, filed on Nov. 20, 2008, the contents of which is incorporated herein by reference.

BACKGROUND AND SUMMARY

The present disclosure relates to a process and a system for the nondestructive determination of the quality of a weld seam. The present disclosure also relates to a welding device to produce a weld seam.

Various processes and systems for the nondestructive assessment of the quality of weld seams are known from prior art. During ultrasonic examinations, for example, acoustic pulses are sent through a weld seam of a component, whose resulting echoes are analyzed by way of a propagation time delay. Conclusions concerning the quality of the weld seam can also be drawn from measuring the geometry of weld seams. In particular, laser triangulation is used for this purpose. Additional known techniques are, for example, eddy current methods or the weld seam characterization by means of x-ray radiation.

The use of the above-mentioned quality control process depends on factors, such as the type of defect to be detected and the accessibility of the weld seam. Despite the diversity of known nondestructive checking methods, destructive control checking procedures frequently continue to be used.

The above-mentioned processes for determining the quality of weld seams have the disadvantage that they cannot be carried out during the welding process. Also, the time demand of these examining procedures is usually greater than the cycle time of the welded-together components, which makes a checking of each individual component almost impossible. In addition, not all types of defects can be detected by means of many of the above-mentioned methods. The information content of existing analyzing processes for characterizing weld seams generally lacks data concerning the so-called lack of fusion. Such a defect may occur even in the case of identical electric operating values of the welding control.

The present disclosure relates to a process and a system for the nondestructive determination of the quality of weld seams. The present disclosure also relates to a welding device by which the quality of the weld seams can be checked on each of the welded components without having to extend the cycle times.

The process for the nondestructive quality determination of weld seams comprises the process steps of: providing a first and a second component; connecting the first and second components by a weld seam produced by a welding operation; measuring a surface temperature of the weld seam and surface temperatures of areas of the first and second components adjacent to the weld seam that were heated by the welding operation; establishing a location-dependent profile from the measured surface temperature; and comparing the location-dependent profile with a desired profile. The system for carrying out the process for the non-destructive determination of the quality of a weld seam according to the above process steps comprises a measuring device to measure the surface temperatures and an analyzing unit to establish the location-dependent profiles and to compare the location-dependent profiles with the desired profile. The system also includes a welding device, wherein the welding device is a movable tool and the measuring device is movable at a constant distance behind the movable tool producing the weld seam.

When materials are joined by welding operations, energy in the form of heat is introduced into the surrounding material by way of the weld seam. The transfer of this heat into the surroundings of the weld seam can be observed by means of the surface temperature. The coupling-in or efficiency of the heat conduction is a direct function of weld seam parameters, such as the connection to the surrounding material, the position of the weld seam relative to the components to be joined as well as the initial gap measurement or the orientation of the components to be joined relative to one another. A quality determination of the weld seam can therefore be carried out in a reliable manner by the process according to the present disclosure. Information concerning fusion penetration, the most important parameter for the examination of a weld seam with respect to an existing lack of fusion, as well as information concerning root defects and through-burning can only by obtained in connection with the analysis of areas adjacent to a weld seam. Since, in addition, surface temperatures can be measured rapidly, all welded components can be subjected to a quality control, so that the risk of forwarding defective components resulting only from sampling can be excluded.

The temperature measuring takes place in a non-contact manner by detecting the emitted thermal radiation. Such non-contact temperature measuring is carried out by using a detector, such as an infrared camera having a detector, by which a rapid and reliable temperature measurement can be obtained. Matrix, line or individual detectors may be used.

The detection of the thermal radiation takes place by a heat radiation detecting detector which moves along the weld seam at the same speed as the tool producing the weld seam, such as a welding head. As a result, it is ensured that the same time difference exists for each point of the weld seam between its production and the temperature determination. A kinematic reversal, that is, an arrangement with a stationary welding head, a stationary detector and components passing through is also possible.

Other aspects of the present disclosure will become apparent from the following descriptions when considered in conjunction with the accompanying drawings.

BRIEF DESCRIPTION OF THE DRAWINGS

FIG. 1 is a perspective view of an embodiment of a system for the nondestructive quality determination with two components connected by a weld seam, in accordance with the present disclosure.

FIG. 2 is a view of an arrangement of a detector with respect to two components connected by a weld seam, in accordance with the present disclosure.

FIG. 3 shows two views in which two components are connected in different fashions by a weld seam and also shows respective heat transfer diagrams resulting from each connection.

DETAILED DESCRIPTION

By a process for the nondestructive determination of the quality of a weld seam connecting a first component 1 and a second component 2, a reliable quality determination of the weld seam is achieved. The quality determination takes place parallel to the welding operation, so that a quality determination of all produced weld seams 3 is possible. A joining of more than two components by a weld seam is within the scope of the present disclosure.

As suggested in FIG. 1, a measuring of surface temperatures of the weld seam 3 produced during an immediately preceding welding operation as well as of the areas of the first component 1 and of the second component 2 which are adjacent to the weld seam 3 and are heated by the welding operation is carried out in accordance with the present disclosure. The surface temperatures of areas of the first component 1 and of the second component 2 adjacent to the weld seam 3 depend on the efficiency of the thermal conduction from the weld seam 3 into the surroundings of the weld seam 3. The thermal conduction is a direct function of weld seam parameters, such as the connection to the material adjoining the weld seam 3, the position of the weld seam 3 relative to the components 1, 2 to be joined but also of initial conditions, such as a gap measurement or the orientation of the components 1, 2 relative to one another.

In a step of the process, a location-dependent heat profile is established from the measured surface temperatures. This heat profile is then compared with a desired profile. The desired profile reflects an ideal condition of two components 1, 2 optimally connected by a weld seam 3.

FIG. 3 shows such a comparison between a weld seam connection with an optimal connection surface, as shown in the upper illustration and graph of FIG. 3 and a poor connection with a reduced connection surface, as shown in the lower illustration and graph of FIG. 3. The views on the left side of FIG. 3 show possible joining geometries of the two components 1, 2 connected by a weld seam 3. In the upper left view, weld seam 3 is visible that has an optimal connection surface to the respective components 2, 3 while, in the lower left view, the weld seam 3 has pushed itself partially between the two components 1, 2, so that the connection surface of the weld seam 3 is reduced, particularly with respect to the second component 2. When the surface temperatures of this arrangement are now measured, particularly perpendicular to a longitudinal dimension of the weld seam 3, a heat profile is obtained, as illustrated in the diagrams on the right side of FIG. 3. The diagrams are divided into three zones a, b and c, wherein: Zone a indicates the continuous heat transfer at the welding root; Zone b shows the radiation intensity in the area of the welding fusion; and Zone c shows the heat transfer in the connection to the second component 2. A significant change of the heat transfer is indicated, particularly in Zone c while the connection surface is small, which can be recognized by the considerable drop of the radiation intensity curve in the lower diagram of FIG. 3.

The temperature measurement itself takes place in a non-contact manner by the detection of the emitted thermal radiation. For this purpose, a measuring device 4 is used which has a detector 6 that is sensitive in the infrared spectral region, for example, as a component of an infrared camera. This detector 6 is constructed as a CCD sensor 6, which is constructed as a line sensor or matrix sensor. The sensitivity of sensor 6 for this field of application is in the close infrared spectral region at a wavelength of, for example, 0.7 to N 5 μm, and also, for example, at 1 to 3 μm.

Depending on the desired spatial resolution or width of weld seam 3, as illustrated in FIG. 2, an objective lens 7 is selected by which the temperature profile or the profile of the emitted radiation is imaged in the above-mentioned spectral region on the sensor 6.

For the quality determination of the entire weld seam 3, the measuring device 4 can be moved at a constant distance behind a movable tool 5 producing the weld seam 3. The measuring device 4 detecting the heat radiation moves at the same speed along the weld seam 3 into a moving direction x as the tool 5 producing the weld seam 3.

By a welding system for producing a weld seam 3 between a first component 1 and a second component 2, according to the present disclosure, which system has a device for carrying out the process for the nondestructive quality determination of a weld seam 3, as described above, a reliable checking of the weld seam 3 becomes possible in the entire range of the weld seam 3. Information concerning the fusion penetration, which is the most important parameter for examining the weld seam 3 with respect to a lack of fusion, can be obtained in that, when determining the quality of the weld seam 3 according to the present disclosure, marginal areas of the mutually welded-together components 1, 2 adjacent to the weld seam are also taken into account when analyzing the measurement. An analyzing unit 9, as shown in FIG. 1, is used for establishing the location dependent temperature profiles and comparing them to desired profiles.

Although the present disclosure has been described and illustrated in detail, it is to be clearly understood that this is done by way of illustration and example only and is not to be taken by way of limitation. The scope of the present disclosure is to be limited only by the terms of the appended claims.

The invention claimed is:

1. A process for the non-destructive determination of the quality of a weld seam, the process steps comprising:
   providing a first and a second component;
   connecting the first and second components by a weld seam produced by a welding operation;
   measuring a surface temperature of the weld seam and surface temperatures of areas of the first and second components adjacent to the weld seam that were heated by the welding operation;
   establishing a location-dependent heat profile from the measured surface temperatures;
   comparing the location-dependent heat profile with a desired profile;
   wherein the temperature measuring takes place perpendicular to a longitudinal dimension of the weld seam;
   wherein the temperature measuring takes place in a non-contact manner by detection of the emitted heat radiation;
   wherein the temperature measuring takes place by a measuring device which detects the heat radiation, in a line-by-line manner, emitted by the weld seam and the areas of the first component and the second component adjacent to the weld seam; and
   wherein the measuring device detecting the heat radiation moves at the same speed along the weld seam as a tool producing the weld seam.

2. The process according to claim 1, wherein the line-by-line manner of detection of the heat radiation takes place perpendicular to a longitudinal dimension of the weld seam.

3. A system for carrying out a process for the non-destructive determination of the quality of a weld seam, the system comprising:
   a measuring device to measure the surface temperatures;
   an analyzing unit to establish the location-dependent heat profile and to compare the location-dependent heat profile with the desired profile;
   wherein the measuring device includes a detector to detect heat radiation;
   wherein the measuring device is movable along the weld seam;
   further comprising a welding device to produce the weld seam between the first and second components; and wherein the welding device is a movable tool and the measuring device is movable at a constant distance behind the movable tool producing the weld seam.

4. The system according to claim 3, wherein the detector is constructed as a line sensor or as a matrix sensor.

5. The system according to claim 3, wherein the detector includes a spectral sensitivity in a close infrared region.

6. The system according to claim 3, wherein the detector is constructed as a CCD sensor.

7. The system according to claim 6, wherein the measuring device includes an objective lens to image emitted radiation onto the CCD sensor.

\* \* \* \* \*